United States Patent [19]
Hollister

[11] Patent Number: 5,490,503
[45] Date of Patent: Feb. 13, 1996

[54] SUCTION CATHETER HAVING MULTIPLE VALVES AND COLLET ASSEMBLY

[75] Inventor: William H. Hollister, East Sullivan, N.H.

[73] Assignee: Smiths Industries Medical Systems, Inc., Keene, N.H.

[21] Appl. No.: 235,479

[22] Filed: Apr. 29, 1994

[51] Int. Cl.⁶ ............................................. A61M 25/01
[52] U.S. Cl. ....................... 128/205.12; 128/207.14; 128/207.15; 128/207.16; 128/200.26; 604/171; 604/119; 604/267
[58] Field of Search ..................... 128/207.14, 207.15, 128/207.16, 207.17, 200.16, 200.26; 604/171, 119, 192, 263, 267

[56]  References Cited

U.S. PATENT DOCUMENTS

| 3,991,762 | 11/1976 | Radford | 128/276 |
|---|---|---|---|
| 4,569,344 | 2/1986 | Palmer | 128/207 |
| 4,638,539 | 1/1987 | Palmer | 29/157 |
| 4,696,296 | 9/1987 | Palmer | 128/207.16 |
| 4,805,611 | 2/1989 | Hodgkins | 128/207.14 |
| 4,825,859 | 5/1989 | Lambert | 128/202.16 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,872,579 | 10/1989 | Palmer | 128/207.12 |
| 4,938,741 | 7/1990 | Lambert | 604/19 |
| 4,967,743 | 11/1990 | Lambert | 128/202.16 |
| 4,981,466 | 1/1991 | Lambert | 604/19 |
| 5,025,806 | 6/1991 | Palmer | 128/203.12 |
| 5,029,580 | 7/1991 | Radford | 128/207.14 |
| 5,060,646 | 10/1991 | Page | 128/207.14 |
| 5,065,754 | 11/1991 | Jensen | 128/200.26 |
| 5,073,164 | 12/1991 | Hollister | 604/43 |
| 5,134,996 | 8/1992 | Bell | 128/207.14 |
| 5,254,098 | 10/1993 | Ulrich et al. | 604/171 |
| 5,269,768 | 12/1993 | Cheung et al. | 604/248 |
| 5,300,043 | 4/1994 | Devlin et al. | 604/250 |
| 5,325,850 | 7/1994 | Ulrich et al. | 128/200.26 |
| 5,343,857 | 9/1994 | Schneider et al. | 128/207.14 |
| 5,349,950 | 9/1994 | Ulrich et al. | 128/207.16 |
| 5,354,267 | 10/1994 | Niermann et al. | 128/207.14 |
| 5,375,589 | 12/1994 | Bhatta | 604/267 |
| 5,377,672 | 1/1995 | Kee | 128/207.14 |

FOREIGN PATENT DOCUMENTS 2207736  2/1989  United Kingdom.

Primary Examiner—Kimberly L. Asher
Assistant Examiner—William J. Deane, Jr.
Attorney, Agent, or Firm—Pollock, Vande Sande & Priddy

[57] ABSTRACT

A closed system suction catheter assembly has a protective sleeve enclosing a suction catheter that can be advanced through a patient connecting member coupling the assembly to a tracheal tube. Within the patient connecting member there is an integral valve and wiper seal assembly formed from a one-piece moulding with a central aperture providing the wiper seal and four duck-bill valve arranged around the periphery. The duck-bill valves are of oval shape and have their smaller dimension aligned radially.

5 Claims, 4 Drawing Sheets 5,490,503

SUCTION CATHETER HAVING MULTIPLE VALVES AND COLLET ASSEMBLY

BACKGROUND OF THE INVENTION

This invention relates to suction catheter assemblies.

The invention is more particularly concerned with assemblies of the kind having an aspirating catheter enclosed within a protective, flexible sleeve and which can be advanced through a coupling at one end of the assembly. The coupling has one port connected to a tracheal tube and two further side ports by which ventilation of the patient can take place. In use, the machine end of the catheter is connected to a suction source via a valve. Secretions that build up on the inside of the tracheal tube, the trachea and bronchi can be periodically removed by opening the valve and advancing the catheter through the coupling and down the tracheal tube. The coupling enables ventilation of the patient to continue while suctioning takes place.

One problem with this kind of assembly is that air may enter the sleeve causing it to inflate; this can make subsequent use of the assembly more difficult. A small amount of air will be present in the sleeve as a result of assembly and additional air can be pulled into the sleeve during the negative pressure cycle of sterilization. Air from the ventilation system, during use, can also be forced back into the sleeve. Although a sliding seal with the outside of the catheter can be provided in the coupling, this does not provide a total air seal. Attempts to improve the seal by making it a tighter fit tend to cause an indentation in the catheter, especially when it is stored for prolonged periods or subjected to elevated temperature, such as during sterilization.

Examples of catheter assemblies having an aspirating catheter contained within a sleeve and which can be pushed through a sliding seal in a coupling are described in several patents, such as U.S. Pat. No. 3,991,752 to Radford; U.S. Pat. No. 4,569,344 to Palmer; U.S. Pat. No. 4,638,539 to Palmer; U.S. Pat. No. 4,696,296 to Palmer; U.S. Pat. No. 4,825,859 to Lambert; U.S. Pat. No. 4,834,726 to Lambert; U.S. Pat. No. 4,836,199 to Palmer; U.S. Pat. No. 4,838,255 to Lambert; U.S. Pat. No. 4,872,579 to Palmer; U.S. Pat. No. 4,938,741 to Lambert; U.S. Pat. No. 4,967,743 to Lambert; U.S. Pat. No. 4,981,466 to Lambert; U.S. Pat. No. 5,025,806 to Palmer; U.S. Pat. No. 5,029,580 to Radford; U.S. Pat. No. 5,060,646 to Page; U.S. Pat. No. 5,065,754 to Jensen; U.S. Pat. No. 5,073,164 to Hollister; and GB 2207736 to Hollister. Suction catheter assemblies of this kind are also available from Smiths Industries Medical Systems Inc under the trade mark STERICATH and from Ballard Medical Products Inc under the trade mark TRACHCARE.

One way of preventing the accumulation of air in the sleeve is to provide a small vent that allows air to escape to atmosphere. This, however, is not desirable because it can allow the escape of contaminated material from the assembly onto the user. It has been proposed in U.S. Ser. No. 08/082,016 to provide a separate, one-way valve in the patient coupling that is opened by raised pressure in the sleeve to allow gas to vent from the sleeve into the patient coupling. The need to provide and assemble the valve into the patient coupling adds to the cost, which is undesirable in a disposable product. It is also necessary to provide an effective seal between both the wiper seal and the valve and the housing in which they are contained, further adding to the complexity of assembly and cost.

SUMMARY OF THE INVENTION

It is an object of the present invention to provide an improved suction catheter assembly.

According to one aspect of the present invention there is provided suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of said proximal end of said aspirating catheter; a patient connecting member mounted to surround said aspirating catheter in the vicinity of said distal end of said aspirating catheter; a protective sleeve surrounding at least the majority of the length of said catheter and extending between said vacuum connecting member and said patient connecting member, said protective sleeve being adapted to permit said distal end of the catheter to be extended from said protective sleeve into the patient and to be withdrawn from the patient; and a one-piece integral valve assembly within said patient connecting member, said valve assembly comprising both a wiper seal for engaging the outside of said catheter and at least one one-way valve for permitting gas flow through the valve out of the interior of said sleeve and into said patient connecting member but preventing any substantial gas flow through said valve into said sleeve such that any gas trapped in said sleeve can escape into said patient connecting member through said one-way valve.

The one-way valve is preferably a duck-bill valve, which may be of oval lateral section having a smaller dimension aligned radially of the valve assembly. The valve assembly preferably includes a plurality of one-way valves, such as four valves formed integrally therewith. The wiper seal is preferably located centrally of the valve assembly and the one-way valves are equally disposed around the wiper seal. The valve assembly may have an outer peripheral flange sealed to the patient connecting member. The catheter assembly may include a collet member joined to the patient connecting member, the flange being trapped between the collet member and the patient connecting member. The collet member preferably has an aperture slightly larger than the external diameter of the catheter, the collet member supporting the valve assembly on the proximal side of the integral assembly. The collet member may include a gas passage along the external surface of the catheter opening into the valve. The gas passage may comprise at least one groove along a central bore of the collet and an annular gas channel formed coaxially around a distal end face of the collet.

According to another aspect of the present invention there is provided a suction catheter assembly of the kind for use in removing undesirable fluid from a patient, the catheter assembly comprising an aspirating catheter having a proximal end and a distal end, said distal end being suitable for insertion into a patient; a vacuum connecting member located in the vicinity of said proximal end of said aspirating catheter; a patient connecting member mounted to surround said aspirating catheter in the vicinity of said distal end of said aspirating catheter; a protective sleeve surrounding at least the majority of the length of said catheter and extending between said vacuum connecting member and said patient connecting member, said protective sleeve being adapted to permit said distal end of the catheter to be extended from said protective sleeve into the patient and to be withdrawn from the patient; and a wiper seal with the outside of said catheter and a valve for permitting gas flow out of said sleeve into said patient connecting member but preventing any substantial gas flow through said valve into sleeve, the improvement being that said wiper seal and said valve are provided by the same one-piece integral valve assembly, wherein said valve assembly is a moulding of resilient material, wherein said valve assembly includes a plurality of said valves, and wherein said valve assembly is sealed around an outer edge with the patient connecting member.

A suction catheter assembly according to the present invention, will now be described, by way of example, with reference to the accompanying drawings.

DESCRIPTION OF THE PREFERRED EMBODIMENTS

Figure 1:
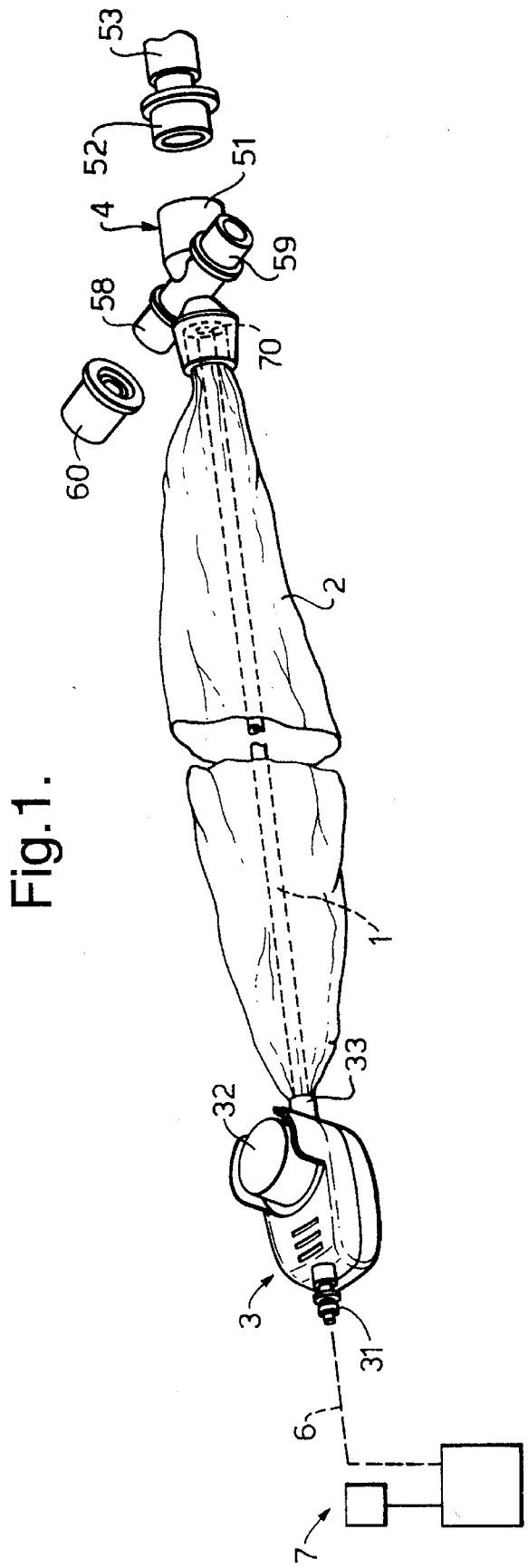
FIG. 1 is a perspective view of the assembly.
Figure 2:
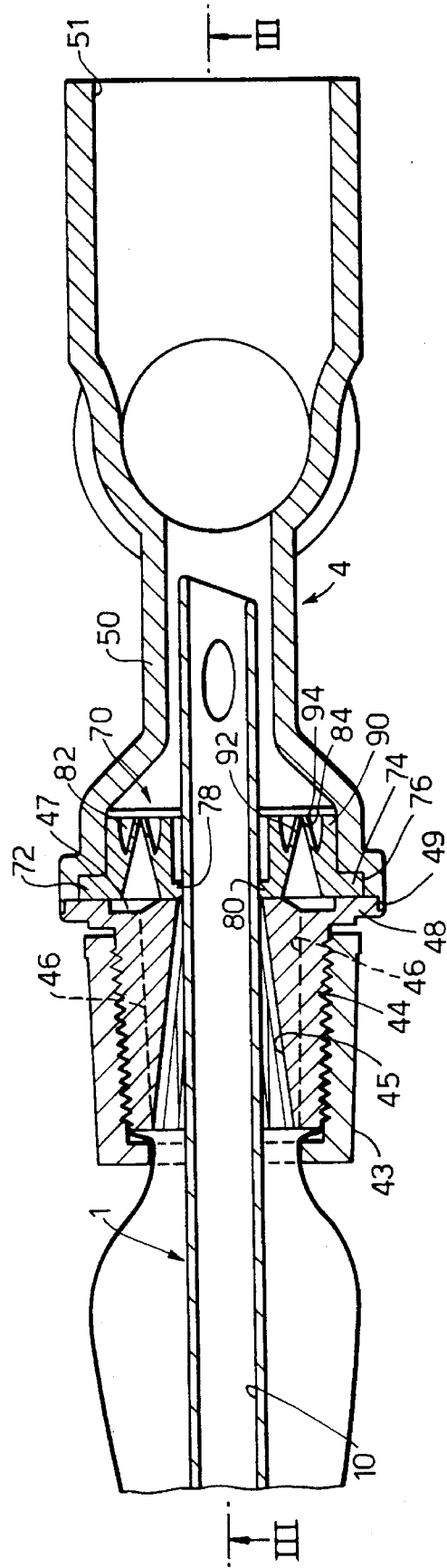
FIG. 2 is a sectional side elevation of the patient connecting member.
Figure 3:
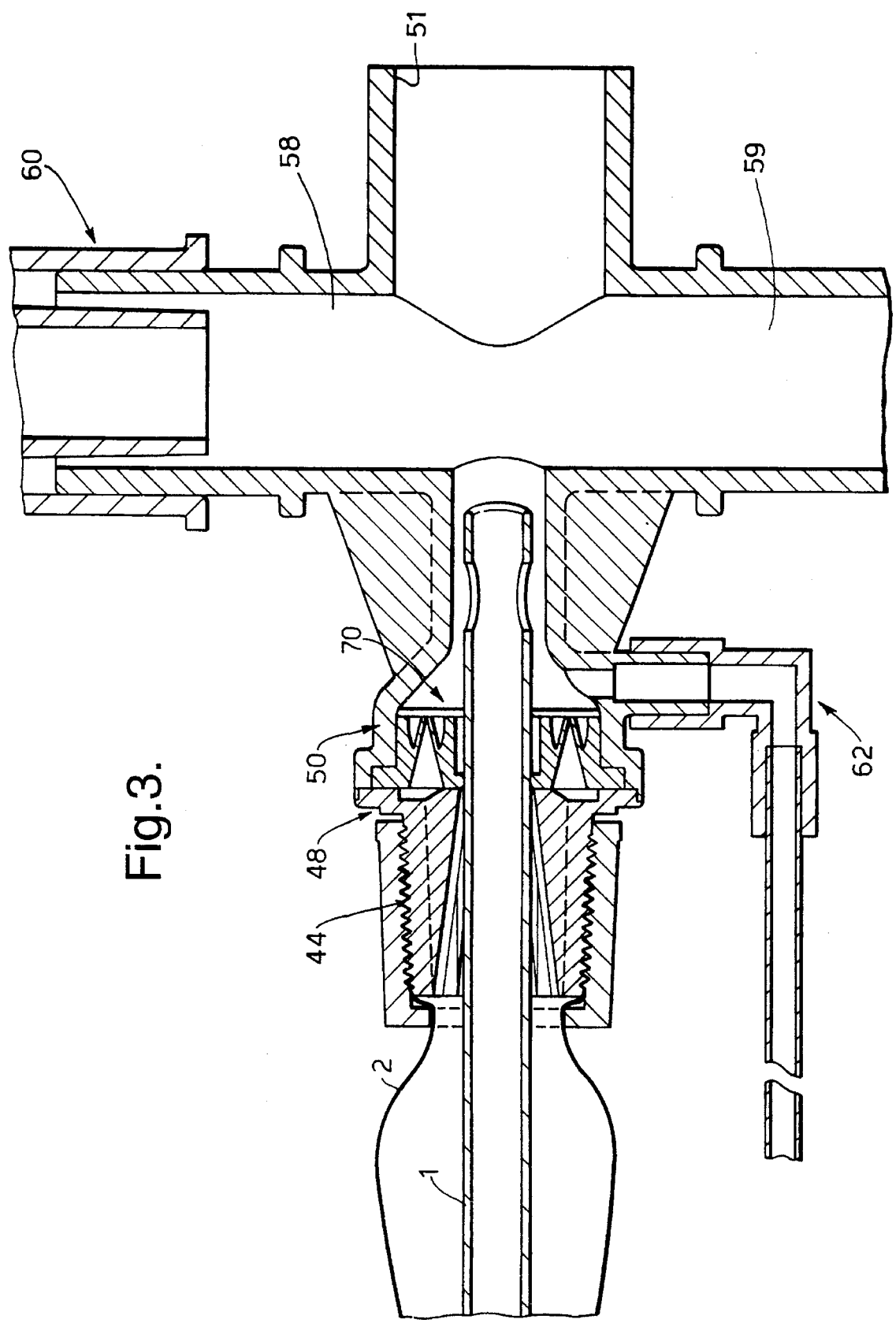
FIG. 3 is a transverse section along the line III—III of FIG. 2.

The suction catheter assembly comprises an aspirating catheter 1 that extends within a flexible, protective sleeve 2 between a vacuum connecting member 3 and a patient connecting member 4.

The aspirating catheter 1 is of conventional construction having an outside diameter of about 4–5 mm and a length of about 55 cm. In the illustrated example, the catheter 1 has a single lumen 10 although catheters with multiple lumens for use in irrigation and/or oxygen supply could be used. At its machine or proximal end, the catheter 1 is secured to the vacuum connecting member 3.

The vacuum connecting member 3 is moulded from a rigid plastics material and has a bore (not shown) extending along it into one end of which the catheter 1 is bonded. The opposite end of the bore extends through a spigot 31, which, in use, is connected to tubing 6 extending to a vacuum or suction source 7. The vacuum connecting member 3 includes a conventional manually-operated valve 32, which normally prevents flow through the connecting member 3 and catheter 1 but which can be pressed down by the user to open the valve and connect the lumen 10 of the catheter to the suction source 7. The valve may be of any conventional kind, or, for example, that described in U.S. Ser. No. 07/965,998.

The proximal end of the sleeve 2 is secured to the vacuum connecting member 3 beneath a collar 33 secured to the distal end of the vacuum connecting member. The distal end of the sleeve 2 is similarly secured to the patient connecting member 4 by means of a collar 43 screwed onto the proximal end of a collet 44. The collet 44 has a central bore 45, which tapers from a large diameter at its proximal end to a smaller diameter aperture, just larger than the catheter 1, at its distal end. The bore 45 is also formed with several grooves 46 that open at the distal end of the collet 44 into a coaxial annular channel 47 in the distal, right-hand end face of the collet. The collet 44 also has a radially-projecting annular flange 48, which is welded into a shallow collar 49 at the proximal end of the main body 50 of the patient connecting member 4.

The patient connecting member 4 is of generally cruciform shape, having a female luer coupling 51 at its distal or patient end, which is aligned with the axis of the connecting member. The coupling 51 is adapted to be connected to a cooperating coupling 52 on the end of a tracheal tube 53.

Two side ports 58 and 59 extend at right angles to the axis of the connecting member, directly opposite one another, about midway along the length of the connecting member. These two side ports 58 and 59 communicate directly with the interior of the coupling 51 and are used in the conventional manner to connect with ventilation apparatus. One port may be used for inhalation gas and the other port used for exhalation gas. Alternatively, one of the ports 58 may be closed by a cap 60 and inhalation and exhalation both be effected through the other port 59. The patient connecting member 4 also includes an irrigation port 62 by which irrigation fluid can be supplied to the outside of the catheter 1.

Figure 4:
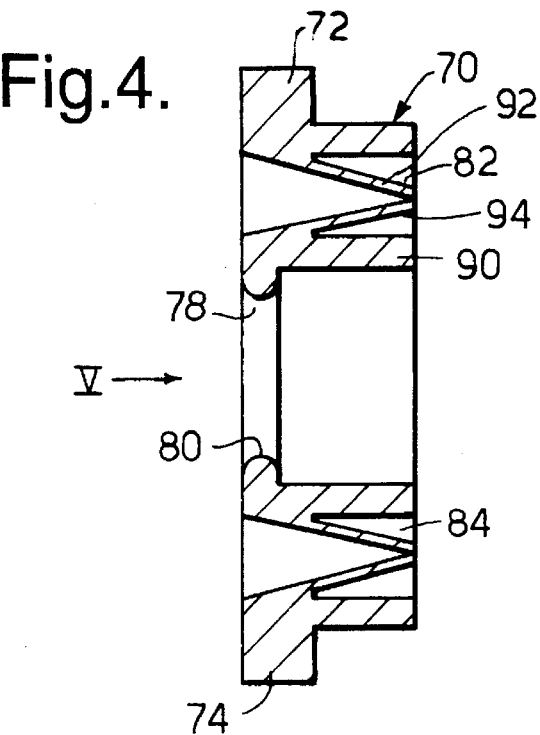
FIG. 4 is a transverse section showing the valve assembly in greater detail.
Figure 5:
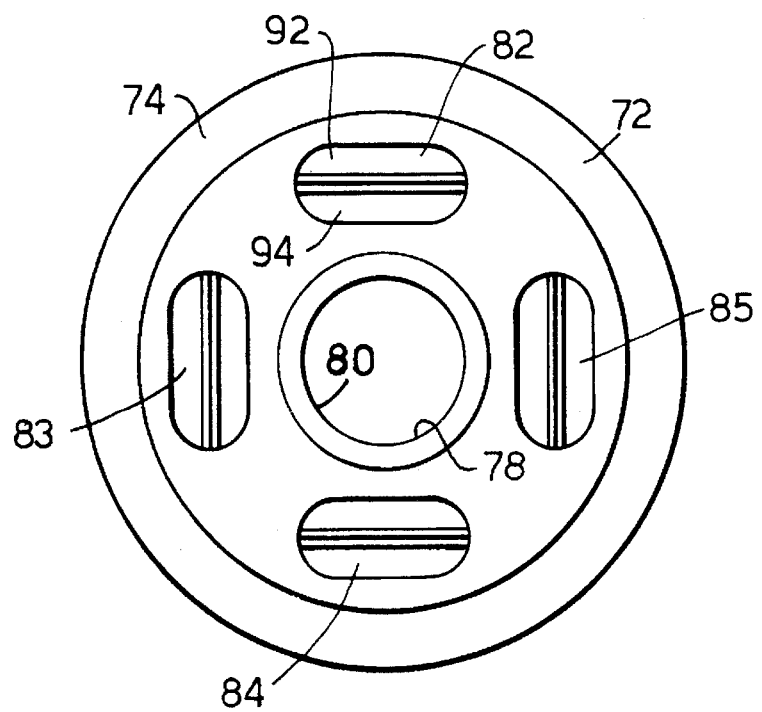
FIG. 5 is view of the assembly shown in FIG. 4 along the line V.

Within the patient connecting member 4 there is a novel wiper seal and one-way valve assembly 70, as shown most clearly in FIGS. 4 and 5. This takes the form of an integral, one-piece moulding of a resilient material such as silicone rubber with a hardness of approximately 40–55 shore A durometer. Alternatively, other materials could be used, such as an injection-moldable styrene-based thermoplastic rubber (for example Santoprene), a compression-moldable neoprene rubber or a compression-moldable butyl rubber. The assembly 70 is of circular shape having, on its proximal side, a planar disc 72 about 18 mm in diameter and 1.5 mm thick. The outer edge of the disc provides a peripheral flange 74 located in a recess 76 at the proximal end of the main body 50 of the connecting member 4 and is trapped in the recess by engagement with the collet 44. The valve assembly 70 extends across the distal face of the collet 44, which supports the proximal side of the valve assembly. A circular aperture 78 extends through the center of the disc 72, the aperture being slightly smaller than the external diameter of the catheter 1 and having a rounded edge, so that the lip 80 of the aperture forms a wiping seal with the catheter. The disc 72 is interrupted by four one-way duck-bill valves 82 to 85, which extend distally and are equally disposed around the central aperture 78. The valves 82 to 85 are moulded integrally with the disc 72 so that they are formed integrally with the wiping seal 80. Each valve 82 to 85 is of identical construction and comprises an outer sleeve 90 of oval shape open at its proximal, left-hand end and closed at its distal, right-hand end by two converging lips 92 and 94. The valves 82 to 85 are oriented as shown in FIG. 5 with their smaller lateral dimension arranged radially so that they occupy the minimum radial distance and thereby enable a maximum proportion of the valve assembly to be occupied by valves. Different numbers of valves could be used and the assembly could have up to about eight valves arranged around its periphery. The construction of duck-bill valves is well known. The lips 92 and 94 are opened by a positive pressure between the lips to allow flow through the valve; pressure externally of the lips causes them to be urged closer together and increases the seal. In the present arrangement it can be seen that an elevated pressure on the proximal, left-hand side of the valves 82 to 85 would allow flow and would open the valves but a pressure on the opposite side would cause the valves to close more tightly.

In operation, the coupling 51 of the connecting member 4 is secured to the coupling 52 on the end of the tracheal tube 53 and its side ports 58 and 59 are connected to a ventilator. The vacuum coupling member 3 is connected to the suction source 7 but, as long as the manual valve 32 remains unactuated, no suction is applied to the catheter 1. While mechanical ventilation takes place, there is raised, positive pressure within the patient connecting member 4 (on the distal side of the valve assembly 70) forcing the duck-bill valves 82 to 85 to close more tightly, thereby blocking gas flow into the sleeve 2. The collet 44 supports the valve assembly 70 against the positive pressure in the patient connecting member 4.

When aspiration of fluid from the trachea or bronchi is required, the user grips the catheter 1 through the sleeve 2 and pushes it forwardly so that the distal, patient end of the catheter is advanced through the connecting member 4 and into the tracheal tube 7. When the catheter 1 has been inserted to the desired depth, the user depresses the valve 32 so that the catheter is connected to the suction source 7 and fluid in the vicinity of the tip of the catheter is sucked into the catheter and removed. During aspiration, ventilation of the patient occurs normally. When aspiration is complete, the catheter 1 is pulled back into the sleeve 2, the assembly remaining attached to the tracheal tube connector 52 so that it can be reused when necessary.

Although the sliding seal of the valve assembly 70 with the catheter 1 is effective to prevent any significant flow of gas into the sleeve 2, there may be some seepage of gas around the catheter, especially when the catheter is being manipulated during aspiration. The valve assembly 70 is, however, effective to allow any gas trapped inside the sleeve 2 to escape when pressure on its proximal side exceeds that on the distal side. The action of gripping the sleeve 2 and advancing the catheter 1 has the effect of compressing any trapped gas in the sleeve, thereby increasing its pressure. The gas flows via the grooves 46 in the collet 44 and the annular channel 47 to the valves 82 to 85, which are thereby opened. In this way, build-up of gas in the sleeve 2 is prevented since the sleeve can vent at relatively low pressure. Because the venting occurs into the connecting member 4, the vented gas is carried to the ventilation system without any risk of cross contamination to the clinician.

The valve assembly 70 could be provided in one part of a patient connecting member, with the side ports 58 and 59 and the female luer coupling 51 being provided in a separate part that is coupled together with the first part during use.

Because the assembly 70 comprises both the valves 82 to 85 and the wiper seal 80 it is moulded as a single piece with a low cost of manufacture. It has been found that, even though the wiper seal and the valves serve different functions, they can operate effectively when moulded from the same material. Installation of the assembly 70 in the patient connecting member 4 is a simple, single step operation, which can be carried out rapidly at low cost. It is only necessary to make a single seal with the connecting member, around the flange 74, thereby increasing the integrity and reliability of the suction catheter.

Various modifications are possible. For example, the assembly might include any number of one or more duckbill valves. The throughput of the valve or valves should be sufficient to allow air to flow rapidly out of the sleeve 2 when it is gripped to advance the catheter, preferably without allowing ballooning of the sleeve. If one valve were used, this would have to be larger than the multiple valves in the present embodiment, to provide the necessary throughput. By using multiple valves, these can be equally distributed around the wiper seal enabling the patient connecting member to have a compact configuration.

What I claim is:

1. A suction catheter assembly for use in removing undesirable fluid from a patient, the catheter assembly comprising:

an aspirating catheter having a proximal end and a distal end, said distal end being suitable for insertion into a patient;

a vacuum connecting member located in the vicinity of said proximal end of said aspirating catheter;

a patient connecting member mounted to surround said aspirating catheter in the vicinity of said distal end of said aspirating catheter;

a protective sleeve surrounding at least the majority of the length of said catheter and extending between said vacuum connecting member and said patient connecting member, said protective sleeve being adapted to permit said distal end of the catheter to be extended from said protective sleeve into the patient and to be withdrawn from the patient; and a one-piece integral valve assembly within said patient connecting member, said valve assembly comprising both a wiper seal for engaging the outside of said catheter and at least one one-way valve for permitting gas flow through the valve out of the interior of said sleeve and into said patient connecting member but preventing any substantial gas flow through said valve into said sleeve such that any gas trapped in said sleeve can escape into said patient connecting member through said one-way valve;

wherein said valve assembly includes a plurality of one-way valves formed integrally therewith.

2. A suction catheter according to claim 1, wherein said valve assembly includes four one-way valves.

3. A suction catheter assembly according to claim 1, wherein said wiper seal is located centrally of said valve assembly and said one-way valves are equally disposed around said wiper seal.

4. A suction catheter assembly for use in removing undesirable fluid from a patient, the catheter assembly comprising:

an aspirating catheter having a proximal end and a distal end, said distal end being suitable for insertion into a patient;

a vacuum connecting member located in the vicinity of said proximal end of said aspirating catheter;

a patient connecting member mounted to surround said aspirating catheter in the vicinity of said distal end of said aspirating catheter;

a protective sleeve surrounding at least the majority of the length of said catheter extending between said vacuum connecting member and said patient connecting member, said protective sleeve being adapted to permit said distal end of the catheter to be extended from said protective sleeve into the patient and to be withdrawn from the patient;

a one-piece integral valve assembly within said patient connecting member, said valve assembly comprising both a wiper seal for engaging the outside of said catheter and at least one one-way valve for permitting gas flow through the valve out of the interior of said sleeve and into said patient connecting member but preventing any substantial gas flow through said valve into said sleeve such that any gas trapped in said sleeve can escape into said patient connecting member through said one-way valve; and wherein said valve assembly has an outer peripheral flange, with said flange being sealed to said patient connecting member;

said suction catheter assembly further includes a collet member joined to said patient connecting member, and said flange is trapped between the collet member and said patient connecting member;

wherein said collet member has a central aperture slightly larger than the external diameter of said catheter, and supports said valve assembly on the proximal side of said integral valve assembly;

wherein said collet member includes a gas passage along the external surface of said catheter, said gas passage opening into each said valve; and wherein said gas passage comprises one groove along a central bore of the collet and an annular gas channel formed coaxially around a distal end face of the collet.

5. A suction catheter assembly for use in removing undesirable fluid from a patient, the catheter assembly comprising:

an aspirating catheter having a proximal end and a distal end, said distal end being suitable for insertion into a patient;

a vacuum connecting member located in the vicinity of said proximal end of said aspirating catheter;

a patient connecting member mounted to surround said aspirating catheter in the vicinity of said distal end of said aspirating catheter;

a protective sleeve surrounding at least the majority of the length of said catheter extending between said vacuum connecting member and said patient connecting member, said protective sleeve being adapted to permit said distal end of the catheter to be extended from said protective sleeve into the patient and to be withdrawn from the patient;

a one-piece integral valve assembly within said patient connecting member, said valve assembly comprising both a wiper seal for engaging the outside of said catheter and at least one one-way valve for permitting gas flow through the valve out of the interior of said sleeve and into said patient connecting member but preventing any substantial gas flow through said valve into said sleeve such that any gas trapped in said sleeve can escape into said patient connecting member through said one-way valve; and a collet member joined to said patient connecting member;

said collet member having a central aperture slightly larger than the external diameter of said catheter;

wherein said valve assembly has an outer peripheral flange, which is trapped between the collet member and said patient connecting member at the proximal side thereof; and wherein said collet member forms a gas passage along the external surface of said catheter, said gas passage opening into said valve and including a groove formed along a central bore of the collet and an annular gas channel formed coaxially around a distal end face of the collet.

* * * * *